United States Patent [19]

Berman et al.

[11] 4,040,959

[45] Aug. 9, 1977

[54] MULTI-PURPOSE BLOOD BAG

[76] Inventors: Irwin R. Berman, 1155 Park Ave., New York, N.Y. 10028; Ira M. Nathan, Old Forge Drive, Carmel, N.Y. 10512

[21] Appl. No.: 698,569

[22] Filed: June 22, 1976

[51] Int. Cl.$^2$ .............. B01D 33/02; B04B 3/00
[52] U.S. Cl. ................. 210/78; 23/292; 128/214 R; 128/DIG. 5; 210/83; 210/360 R; 210/515; 210/516; 210/537; 210/540; 210/DIG. 23; 222/94
[58] Field of Search ............ 128/272, 227, 214 R, 128/214 D, 272.1, DIG. 5; 23/292; 222/94; 210/78, 83, 513, 515, 516, 532, 537, 538, 540, DIG. 23, 360 R

[56] References Cited
U.S. PATENT DOCUMENTS

| | | | |
|---|---|---|---|
| 2,848,995 | 8/1958 | Ryan | 210/24 R |
| 3,187,750 | 6/1965 | Tenczar | 128/272 |
| 3,375,824 | 4/1968 | Krakauer et al. | 128/272.1 |
| 3,513,976 | 5/1970 | James | 210/78 |
| 3,520,471 | 7/1970 | Faust | 128/272 |
| 3,545,671 | 12/1970 | Ross | 128/272 |
| 3,554,256 | 1/1971 | Anderson | 128/272 |
| 3,800,947 | 4/1974 | Smith | 210/DIG. 23 |
| 3,911,918 | 10/1975 | Turner | 128/214 R |
| 3,949,744 | 4/1976 | Clarke | 128/214 R |

*Primary Examiner*—Frank W. Lutter
*Assistant Examiner*—Frank Sever
*Attorney, Agent, or Firm*—Blum, Moscovitz, Friedman & Kaplan

[57] ABSTRACT

A bag for the separation of components in blood by gravitational settlement or centrifugation, has an upper chamber and a lower chamber connected by a slender neck, there being access conduits to each of said chambers and said neck. The bag is so dimensioned that for blood having a normal hematocrit the interfaces between packed red cells and the buffy coat and between the buffy coat and the plasma will lie within the neck. The neck can then be clamped off or otherwise sealed to separate the phases sharply and to permit virtually 100% recovery of the plasma and the packed red cells. In a second embodiment, the buffy coat can be isolated and seals within the system opened to permit intermixing of the plasma and the packed red blood cells under completely sterile conditions. A special support makes it possible for the blood bag to be subjected without distortion to centrifugation.

21 Claims, 4 Drawing Figures

MULTI-PURPOSE BLOOD BAG

BACKGROUND OF THE INVENTION

Conventional storage of whole blood is accompanied by the accumulation of microaggregates in blood which are thought to be harmful when transfused (pulmonary microembolism). This particulate matter derives principally from dead or disintegrating white blood cells and platelets which have a much shorter life (3 to 5 days) than oxygen-carrying red cells. Non-viable platelets and leucocytes are unnecessary in the context of stored-blood transfusion. Current transfusion practice relies upon microfiltration of this debris between the container and the patient during the process of transfusion for removal of this solid matter. This is a moderately expensive and imprecise procedure. Moreover, failure to remove this debris completely can have serious consequences.

As an example of such consequences, febrile reactions and sensitivity to transfused blood are frequently related to transfused white blood cells or platelets which are non-functional after storage. Current methodology for their total removal from transfused blood is time-consuming, relatively costly and cumbersome and wasteful of up to 25% of the red cell mass.

A further point to be considered is that not all patients require whole blood transfusion. Many patients specifically require only plasma, red cells, white cells or platelets. Hence, fractions from any given unit ideally should be capable of serving more than one patient if necessary. Although current component methodology for this purpose is relatively well-defined, separation of components is usually irreversible once it is performed.

A number of attempts have been made to overcome the difficulties described above, one such attempt being described by W. C. James in U.S. Pat. No. 3,513,976.

James shows two rigid flasks, each having a conical end, the conical ends being joined by a neck. The objective of this device is similar to that of subject invention, namely a device which can be subjected to settling in order to establish interfaces which lie within the neck; adjustment can be made by adding mercury to the bottom flask through a tube or by removing mercury originally present from the bottom flask. The separated white cells or plasma can then be removed through a pipette. Clearly, this is an undesirable method because of inevitable admixture during pipetting, breach of sterile technique in blood handling and the obvious hazards of mercury contact. Although not so stated in the patent, it is evident that James' flasks are rigid; at column 2, line 50, it is stated that the device may be made of glass or any other material having the required property of transparency. This description could include a transparent plastic film, but the entire description reads in general on a rigid structure.

G. R. Ryan in U.S. Pat. No. 3,761,408 shows a flexible plastic bag in a transfusion apparatus. In his FIG. 9 the bag is shown separated into two portions by clamps, so that plasma and cells can be withdrawn separately. In addition, in column 3, line 5 and 6, Ryan states that heat sealing may be used instead of the clamps. (1) However, white blood cells and platelets cannot be immediately and aseptically segregated or removed from blood; (2) blood components cannot be either stored in or transfused directly from individual parent chambers to patient; (3) the option for component or whole blood therapy cannot be maintained throughout the period of blood storage and (4) the capacity for in-container washing is not afforded.

As is evident, although the concept of a plastic bag for use in the separation of whole blood has been disclosed and the concept of a design which facilitates separation of the components has also been disclosed, although with respect to rigid apparatus, it would be highly desirable that there by made available a plastic bag which is low in cost and which can be subjected to centrifugation to facilitate separation of various components. Moreover, the design of the bag should be such as to make it possible to recover virtually the entire quantities of red blood cells in the original volume of blood. Further, the design should be such that any of the components can be taken off separately, the components referred to being plasma, buffy coat with platelets, and packed red cells, and that, where desired, red blood cells in combination with plasma can be obtained. Finally, the design should be such that microfiltration for the purpose of removal of debris from the separated products should not be necessary.

SUMMARY OF THE INVENTION

A blood bag for the separation of blood into plasma, buffy coat, with platelets (the combination hereinafter referred to as "buffy coat") and red blood cells, is made of flexible, transparent plastic, the bag consisting essentially of upper and lower chambers connected by a neck. Each of the chambers and the neck has sealed conduits attached thereto for the purposes of filling the bag with blood and for removing components after separation, access for performance of these steps being had by means of hypodermic needles which pierce the seals. The chambers are sized relative to each other and the neck is so sized that after separation is effected, the buffy coat will lie entirely within the neck, but with some margin. If the interfaces between the phases do not lie entirely within the neck, adjustments can be made by applying pressure to the appropriate chamber. The neck can then be sealed off above and below the buffy coat, making all three phases readily available. It is especially significant that the plasma and the red blood cells are uncontaminated with the buffy coat or other debris resulting from decomposition of same.

A special support makes it possible to centrifuge the bag, the support holding the chambers apart during centrifugation.

In a second embodiment, after sealing off the buffy coat within the neck, a second neck can be opened to connect the upper and lower chambers and thus permit intermixing of the plasma with the red blood cells, where such a mixture is desired for transfusion.

The second neck is sealed off during the separation process, and special means are provided for opening the seals subsequent to sealing off the buffy coat within the first neck. A safety clip is provided for preventing accidental opening of the seals in the second neck during manipulation and centrifugation.

Separation is effected either by gravity settlement or by centrifugation. Separation by centrifugation is preferred due to its rapidity. Further, if differential centifugation is carried out starting at a relatively low velocity, two interfaces result, these being the boundary between the packed red cells and the buffy coat and between the buffy coat and the platelet-rich plasma. Where only the packed red cells are required, the procedure can be stopped at this point. To separate the platelets from the plasma, the centrifugation is carried out at high velocity and the platelets separate downwardly from the plasma.

Formation of the interfaces is facilitated by the shape of the chambers, the bottom of the upper chamber and the top of the lower chamber sloping toward each other at the first neck.

Accordingly, an object of the present invention is a blood bag for separating the components of the whole blood, namely, plasma, buffy coat and red blood cells, the bag being shaped so that it is convenient to isolate the buffy coat from the other components, thereby making it possible to obtain both plasma and packed red blood cells free of buffy coat components.

Another object of the present invention is a blood bag which can separate whole blood into its components and afford practically 100% utilization of the plasma and red blood cells thus obtained. A further object of the present invention is a blood bag which can be subjected to centrifugation for the purpose of separating whole blood into its components.

An important object of the present invention is a blood bag in which the components of whole blood can be separated from each other with efficiency high enough so that microfiltration for the purpose of removing buffy coat components immediately prior to transfusion is unnecessary.

An important object of the present invention is a method of separating blood into its components through the use of an appropriately shaped blood bag. f A significant object of the present invention is a method of separating packed red blood cells from whole blood where the packed red cells are completely free of buffy coat components and plasma, such a separation being desired when only the packed red blood cells are needed.

Still other objects and advantages of the invention will in part be obvious and will in part be apparent from the specification.

The invention accordingly comprises the several steps and the relation of one or more of such steps with respect to each of the others, and the apparatus embodying features of construction, combination of elements and arrangements of parts which are adapted to effect such steps, all as exemplified in the following detailed disclosure, and the scope of the invention will be indicated in the claims.

BRIEF DESCRIPTION OF THE DRAWING

For a fuller understanding of the invention, reference is had to the following description taken in connection with the accompanying drawings, in which.

DESCRIPTION OF THE PREFERRED EMBODIMENTS

Figure 1:
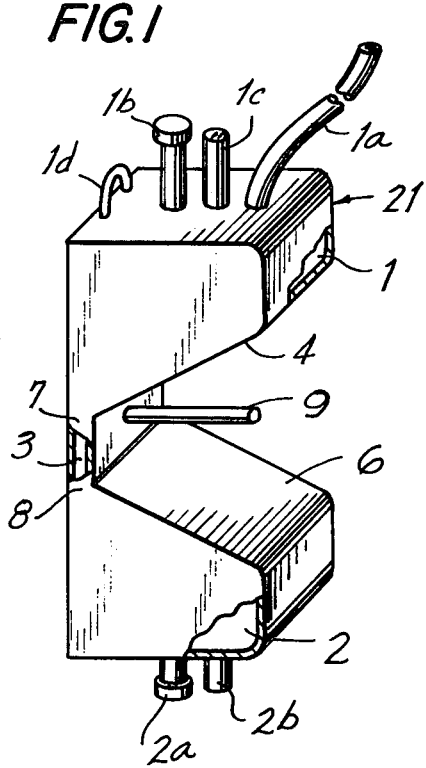
FIG. 1 is a view in perspective of a blood bag in accordance with the present invention.

A device in accordance with the present invention is indicated generally in FIG. 1 by the reference numeral 21, the device being a flexible transparent bag divided into upper and lower chambers 1 and 2, connected by a narrow vertical section or neck 3. Chamber 1 has a conventional donor tube or port 1a, transfusion, access ports 1b and 1c and hanger 1d. Chamber 2 has conventional transfusion and access ports 2a and 2b. All donor transfusion and access ports are sealed or sealable, such seals being effected by appropriate caps, plastic discs, or by knotting of donor tube 1a.

Neck 3 is open, allowing free communication between chambers 1 and 2. This neck is of such a shape that it can be sealed off by clamping (or heat or ultrasound) proximate to its upper and lower ends. The chambers are so sized that when blood is collected in the bag and allowed to settle or centrifuge, the interfaces between plasma, buffy coat and red cells will lie within the open neck 3. In the event that the levels of these interfaces do not fall within the neck (e.g., abnormal hematocrit) the level may be adjusted by application of pressure to the appropriate end of the bag. The pressure may be applied manually or by a roller, etc. Following sedimentation of the fractions or slow centrifugation within the container, followed by any necessary adjustment of the interfaces, the red cell mass may be isolated from the buffy coat and plasma by occlusion across the lower end of the neck making certain that the separation is within the red cell mass so that no buffy coat is included in the red cell phase. Following this procedure by rapid centrifugation results in the sedimentation of both platelets and leucocytes within neck 3, these being the components of the buffy coat. The upper end of the neck may then be occluded and both ends of neck 3 heat-sealed, making certain that the upper sedimentation line is within the plasma phase, thus effecting a permanent exclusion of platelet and leucocyte material responsible for white body reaction and particulate matter in bank blood.

Sharp separation of the blood into the three components is facilitated by the fact that bottom 4 of the upper chamber 1 slopes downwardly toward neck 3 whereas top 6 of the bottom chamber 2 slopes upwardly toward neck 3; in other words, surfaces 4 and 2 slope toward each other as they approach neck 3. It can readily be seen that sloping surface 4 provides a funnel effect for guiding particulate matter such as the buffy coat and the red cells into neck 3. Upwardly sloping surface 6 provides a similar function, during adjustment of the interfaces in the event of an abnormal hematocrit, in which case one or both interfaces may lie within chamber 2, in this case, chamber 2 is compressed and sloping surface 6 guides one or both interfaces, as the case may be, into neck 3.

Generally, the quantity of blood treated will be a "blood unit" having a volume of about 450 cc. Conveniently, the volumes of the neck and lower chamber will be about 5% and 38% of this value, with the upper chamber having a volume of at least 57% of this value. Since the hematocrit of normal blood lies between 35% of 45% and is generally close to 40%, the two interfaces will usually fall within neck 3. If one or both interfaces are outside neck 3, they can be displaced into neck 3 by pressure applied to the appropriate chamber. Neck 3 can then be sealed off proximate to its upper and lower ends 7 and 8, respectively. Since the sealing-off process takes place at regions which are outside the limits of the buffy coat, no part of the undesired solid matter can remain in either the plasma or the packed red blood cell fractions. Subsequently, microfiltration between the blood bag and the recipient during transfusion is unnecessary. If desired, the buffy coat can be removed through tube 9.

Figure 2:
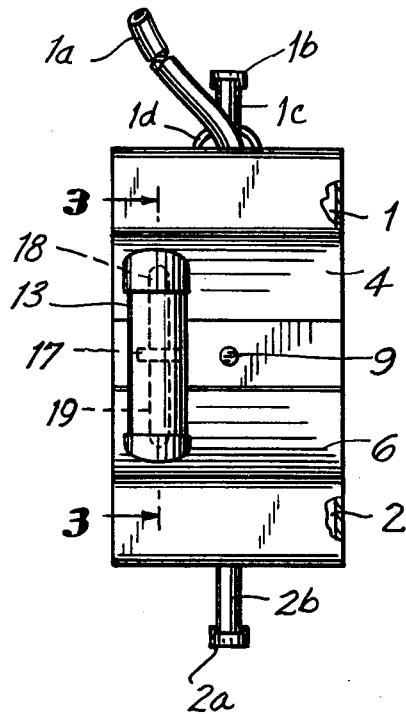
FIG. 2 is a front view of a second embodiment of the invention.
Figure 3:
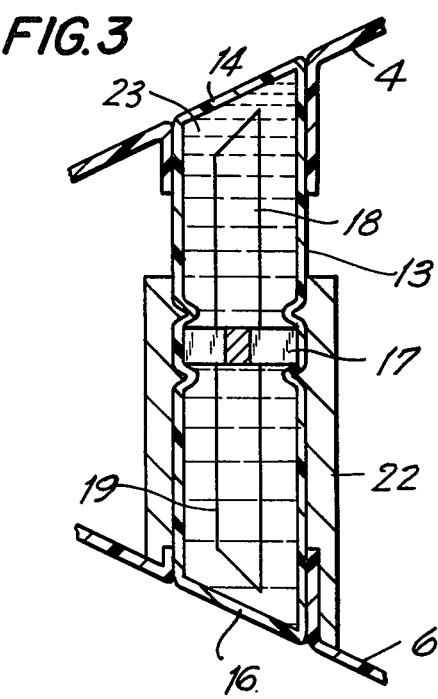
FIG. 3 is a view in enlarged scale along line 3—3 of FIG. 2.
Figure 4:
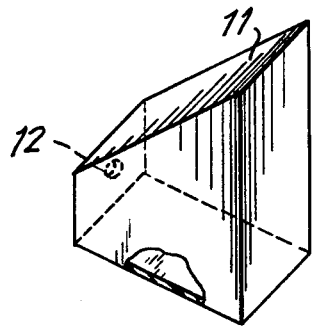
FIG. 4 is a view in perspective of a support for use in combination with the blood bag of FIG. 1.

To prevent collapse of chamber 1 toward chamber 2 during centrifugation, block 11 is positioned in the gap between chambers 1 and 2 during centrifugation. The block 11 can have an aperture 12 therein to receive tube 9. Conveniently, block 11 can be made of a rigid plastic such as polymethylmethacrylate, and, conveniently, may be hollow. Where a second neck such as is shown in FIGS. 2 and 3 is present, block 11 may be appropriately notched (not shown).

An important feature of the design is that throughout the storage life of the blood, the option for whole blood transfusion or specific component administration remains open. In fact, after fractionation and sealing of the neck above and below the buffy coat, the bag can be cut apart to separate the chambers with their individual contents. Each chamber can then be used directly for transfusion therefrom. The packed red cells in the lower chamber can be washed in the conventional manner, through the ports provided.

Where it is desired to transfuse both the plasma and the red blood cell fractions, exclusive of the white blood cells and platelets, of course, then it would be advantageous to be able to recombine the plasma and red blood cell fractions within the blood bag, and thus avoid the possibility of loss of sterility. This objective can be met by introduction of a second neck connecting chambers 1 and 2 as shown in FIGS. 2 and 3. A second neck connecting chambers 1 and 2 is shown in an enlarged sectional view in FIG. 3, wherein the second neck has the reference numeral 13. In order to prevent the buffy coat from entering second neck 13 during the separation process, the upper and lower ends of neck 13 are closed respectively with seals 14 and 16. After separation is effected, the seals must be opened. An example of a device for opening the seals is a piercing means 17 disposed within neck 13, said piercing means 17 having slots or apertures therethrough, or being sized smaller than said neck to provide a path for the flow of liquid. The piercing means 17 may be fitted with knives 18 and 19 for penetration of seals 14 and 16 during handling, and, especially during centrifugation, a support means 22 may be provided, said support means 22 clamping neck 13 immediately above and below the central portion of piercing means 17. To provide against displacement of support means 22 during centrifugation, the bottom end thereof may rest against the top of lower chamber 2. Further, where there is concern for breakage of seal 14 due to the centrifugal pressure generated by the fluid in chamber 1, neck 13 may be filled with a non-deleterious fluid 23 such as normal saline, thereby providing transfer of the pressure exerted by the fluid in chamber 1 to the fluid in chamber 2.

After the fractionating is complete the buffy coat in neck 3 is sealed off, support 22 which can be hinged for easy removal, is separated from neck 13 and piercing means 17 is manipulated by the fingers until it pierces both seals 14 and 16 in succession. Following opening of seals 14 and 16, the bag is tipped back and forth so that fluid will flow back and forth from one chamber to the other, the process being continued until thorough mixture is effected. For this purpose, upper chamber 1 may be larger than 57% of the volume of blood to be treated. Also neck 13 should be of relatively large diameter and the openings made in seals 14 and 16 should also be generously sized to facilitate the mixing process. When mixing is complete, the resultant mixture, which is completely free of unwanted components can then be transfused directly.

As is evident from the structure of the blood bag disclosed herein, it is possible to obtain each of the fractions separately or any pair of the fractions in admixture. Moreover, the buffy coat may be withdrawn through conduit 9 and treated so separate off the platelets for administration to platelet-deficient patients. Also, where only the red blood cells are desired, the separation process can be stopped at the state where the red blood cells are separated from the other fractions. Further, and most important, since neck 3 holds, at most, only five percent of the total volume of the original blood volume, and sealing of the neck can be effected close to the interfaces, the recovery of plasma and packed red blood cells can be virtually 100%, instead of the much lower recoveries obtainable with conventional systems.

In using the blood bag, the bag is prepared by introducing a measured conventional quantity of energy-rich anti-coagulant. The blood unit is introduced through tube 1a which is then sealed as by clips, knot or other conventional means. After carrying out the fractionation as described above, the selected fraction or combination of fractions may be transferred directly to a patient without an intervening filter, the fraction or fractions being withdrawn through the appropriate outlet provided.

A number of different types of plastics can be used. The plastic should be at least translucent so that the position of interfaces is observable. The plastic should also be sealable, for convenience in fabrication, and so that neck 3 can be sealed off proximate but beyond the interfaces. The sealing of neck 3 can be effected by clamping, as aforenoted, by heat or by sonic means.

It will thus be seen that the objects set forth above, among those made apparent from the preceding description, are efficiently attained and, since certain changes may be made in carrying out the above method and in the construction set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A blood bag in combination with a rigid support means, said blood bag of flexible, at least translucent plastic for separation of whole blood into fractions and for direct transfusion therefrom, said bag comprising an upper chamber, a lower chamber, a sealable neck of reduced cross section connecting said upper and lower chambers, said upper and lower chambers and neck cooperating to define a gap when said blood bag is filled with blood, said rigid support means having a shape which generally conforms to the contour of said gap, said support means when positioned in said gap functioning to prevent collapse of said upper chamber toward said lower chamber during centrifugation, means for introducing blood into said blood bag and means for removing fractions of said blood subsequent to separating same, whether by gravity or by centrifugation, said upper and lower chambers and said neck being so sized that when separation of blood of normal range hematocrit into packed red blood cells, buffy coat and plasma is carried out in said bag, the interfaces between said packed red blood cells and said buffy coat and between said buffy coat and said plasma will lie in said neck, said plastic being of a flexibility such that application of pressure to either one of said chambers will move said interfaces toward the other chamber, thereby providing for positioning both of said interfaces within said sealable neck prior to sealing same.

2. The blood bag as defined in claim 1, wherein said neck is adapted for sealing by clamping.

3. The blood bag as defined in claim 1, wherein said blood bag is of a heat-sealable material.

4. The blood bag as defined in claim 1, wherein the volumes of said neck, said lower chamber and said upper chamber are respectively about 5%, 38% and at least approximately 57% of the total volume of blood to be fractionated.

5. The blood bag as defined in claim 1, wherein said upper chamber has a bottom and said lower chamber has a top, said bottom sloping downwardly toward said neck and said top sloping upwardly toward said neck.

6. The blood bag as defined in claim 1, wherein said means for introducing blood into said bag includes a sealable tube.

7. The blood bag as defined in claim 6, wherein said sealable tube is connected to said upper chamber.

8. The blood bag as defined in claim 1, wherein said means for removing fractions includes at least one tube connected to each of said chambers and to said neck, each of said tubes being pierceably sealed, whereby plasma, buffy coat and platelets and packed red cells may be selectively removed from said blood bag subsequent to separation and occlusion of said neck above and below said buffy coat.

9. The blood bag as defined in claim 1, wherein said support means is shaped to conform to said bottom of said upper chamber and said top of said lower chamber.

10. The blood bag as defined in claim 1, wherein said upper and lower chambers and neck are rectangular in cross section.

11. A method of separating whole blood into recoverable fractions, comprising the steps of filling with blood a flexible, at least translucent bag having upper and lower chambers connected by a neck with a gap between said chambers, positioning rigid support means in said gap between said chambers, said upper and lower chambers being sized so that on settling, buffy coat will lie within said neck with blood of normal hematocrit, centrifuging said bag with support means causing packed red cells to separate from said blood, exerting pressure on one of said chambers where necessary to bring the upper surface of said packed red blood cells into said neck and near the bottom thereof, and sealing said neck immediately below said upper surface, thereby making it possible to recover virtually 100% of said packed red blood cells from the blood in said bag.

12. The method of separating whole blood into recoverable fractions as defined in claim 11, further comprising the step of causing the buffy coat to separate from said blood, the volume of said neck being more than adequate to hold said buffy coat, and sealing said neck immediately above said buffy coat, thereby making it possible to recover virtually 100% of said plasma free of said buffy coat and of packed red cells.

13. The method of separating whole blood into recoverable fractions as defined in claim 12, wherein said separation is effected by gravitational settling.

14. The method of separating whole blood into recoverable fractions as defined in claim 12, wherein said separation is effected by differential centrifugation.

15. The method of separating whole blood into recoverable fractions as defined in claim 14, further comprising the step of placing a support means between said upper and lower chambers prior to centrifugation to hold said chambers apart during centrifugation.

16. The method of separating whole blood into recoverable fractions as defined in claim 12, wherein said bag has a second neck connecting said upper and lower chambers, said second neck being openably sealed at the top and bottom thereof prior to separation of any blood components and further comprising the steps of opening said seals subsequent to sealing off said neck containing said buffy coat and mixing said packed red cells and said plasma under sterile conditions by causing said packed red cells and plasma to flow alternately from one chamber to the other through said second neck for subsequent transfusion as whole blood less leucocytes and platelets.

17. The method of separating whole blood into recoverable fractions as defined in claim 12, wherein said blood bag has a second neck connecting said upper and lower chambers filled with a non-deleterious liquid to prevent rupture of a seal due to unbalanced forces during centrifugation.

18. The method of separating whole blood into recoverable fractions as defined in claim 12, further comprising the steps of removing said buffy coat from said bag, and separating the platelets from said buffy coat for administration to a platelet-deficient patient.

19. The method of separating whole blood into recoverable fractions as defined in claim 11, further comprising the step of placing a support means between said upper and lower chambers prior to centrifugation to hold said chambers apart during centrifugation.

20. The method of separating whole blood into recoverable fractions as defined in claim 11, further comprising the step of washing said packed red blood cells within said bag in preparation for transfusion of said red blood cells.

21. A blood bag of flexible, at least translucent plastic for separation of whole blood into fractions and for direct transfusion therefrom, said bag comprising an upper chamber, a lower chamber, a sealable first neck of reduced cross section connecting said upper and lower chambers, a second neck connecting said chambers, means for introducing blood into said blood bag and means for removing fractions of said blood subsequent to separating same, whether by gravity or by centrifugation, said upper and lower chambers and said first neck being so sized that when separation of blood of normal range hematocrit into packed red blood cells, buffy coat and plasma is carried out in said bag, the interfaces between said buffy coat and said plasma will lie in said first neck, said second neck initially having seals at the top and bottom thereof, and containing therein, means to open said seals, said second neck functioning upon the opening of said seals to mix plasma with red blood cells within said bag after separating same, said plastic being of a flexibility such that application of pressure to either one of said chambers will move said interfaces toward the other chamber, thereby providing for positioning both of said interfaces within said sealable first neck prior to sealing same.

* * * * *